(12) United States Patent
Drent et al.

(10) Patent No.: US 7,273,959 B2
(45) Date of Patent: Sep. 25, 2007

(54) CATALYTIC TRIMERIZATION OF OLEFINIC MONOMERS

(75) Inventors: Eit Drent, Amsterdam (NL); René Ernst, Amsterdam (NL)

(73) Assignee: Shell Oil Company, Houston, TX (US)

( * ) Notice: Subject to any disclaimer, the term of this patent is extended or adjusted under 35 U.S.C. 154(b) by 451 days.

(21) Appl. No.: 10/959,561

(22) Filed: Oct. 6, 2004

(65) Prior Publication Data

US 2005/0113622 A1 May 26, 2005

(30) Foreign Application Priority Data

Oct. 10, 2003 (EP) .................................. 03256426

(51) Int. Cl.
*C07C 2/08* (2006.01)
*C07C 2/26* (2006.01)
*B01J 31/00* (2006.01)

(52) U.S. Cl. ........................ 585/514; 585/502; 585/510

(58) Field of Classification Search ................ 585/514, 585/502, 510; 502/103, 104, 162
See application file for complete search history.

(56) References Cited

U.S. PATENT DOCUMENTS

| | | | | |
|---|---|---|---|---|
| 5,195,563 | A | 3/1993 | Brooks ........................ | 138/103 |
| 5,523,507 | A | 6/1996 | Reagen et al. ............... | 585/513 |
| 5,968,866 | A | 10/1999 | Wu ............................. | 502/155 |
| 6,800,702 | B2 | 10/2004 | Wass ........................ | 526/124.3 |
| 2003/0166456 | A1 | 9/2003 | Wass .......................... | 502/102 |
| 2005/0113622 | A1 | 5/2005 | Drent et al. ................. | 585/521 |
| 2006/0235250 | A1 | 10/2006 | De Boer et al. ............ | 585/502 |

FOREIGN PATENT DOCUMENTS

| WO | 02/04119 A1 | 1/2002 |
|---|---|---|
| WO | WO2004056478 | 7/2004 |
| WO | WO2004056479 | 7/2004 |
| WO | WO2004056480 | 7/2004 |
| WO | WO2005123633 | 12/2005 |

OTHER PUBLICATIONS

"High Activity Ethylene Trimerisation Catalysts Based on Diphosphine Ligands," by Anthea Carter, Steven A. Cohen, Neil A. Cooley, Aden Murphy, James Scutt, and Duncan F. Wass, Chem. Commun., 2002, 8, pp. 858-859.
Burgess et al., Stereochemically Matched (and Mismatched) Bisphosphine Ligands: DIP-DIRAMP Hybrids Organometallics, vol. 11, 1992, pp. 3588-3600, p. 3591 Figure 3, compounds 6, 7, 9.

*Primary Examiner*—Caixia Lu

(57) ABSTRACT

A catalyst composition suitable for the trimerization of olefinic monomers, wherein the catalyst composition comprises:
  a) a source of chromium, molybdenum or tungsten;
  b) a ligand of general formula (I);

$$(R^1)(R^2)P—X—P(R^3)(R^4) \qquad (I)$$

wherein:
  X is a bivalent organic bridging group;
  $R^1$ and $R^3$ are independently selected from, hydrocarbyl, substituted hydrocarbyl, heterohydrocarbyl and substituted heterohydrocarbyl groups, with the proviso that when $R^1$ and $R^3$ are cycloaromatic groups they do not contain a polar substituent at any of the ortho-positions;
  $R^2$ and $R^4$ are independently selected from optionally substituted cycloaromatic groups, each $R^2$ and $R^4$ bearing a polar substituent on at least one of the ortho-positions; and
  c) a cocatalyst.

The present invention further relates to a process for the trimerization of olefinic monomers, particularly the trimerization of ethylene to 1-hexene, wherein the process comprises contacting at least one olefinic monomer with the catalyst composition described hereinabove.

18 Claims, No Drawings

CATALYTIC TRIMERIZATION OF OLEFINIC MONOMERS

FIELD OF THE INVENTION

The present invention relates to a catalyst for the trimerization of olefinic monomers. The present invention also relates to a process for the trimerization of olefinic monomers, in particular for producing 1-hexene from ethylene, in the presence of said catalyst.

BACKGROUND OF THE INVENTION

The efficient catalytic trimerization of olefinic monomers, such as the trimerization of ethylene to 1-hexene, is an area of great interest for the production of olefinic trimers of varying degrees of commercial value. In particular, 1-hexene is a valuable comonomer for linear low-density polyethylene (LLDPE). 1-hexene can also be produced by a conventional transition metal oligomerization process, although the trimerization route is preferred as it largely avoids the production of unwanted olefins.

Several different catalytic systems have been disclosed in the art for the trimerization of ethylene to 1-hexene. A number of these catalysts are based on chromium.

U.S. Pat. No. 5,198,563 (Phillips) discloses chromium-based catalysts containing monodentate amine ligands useful for trimerizing olefins.

U.S. Pat. No. 5,968,866 (Phillips) discloses an ethylene oligomerization/trimerization process which uses a catalyst comprising a chromium complex which contains a coordinating asymmetric tridentate phosphane, arsane or stibane ligand and an aluminoxane to produce alpha-olefins which are enriched in 1-hexene.

U.S. Pat. No. 5,523,507 (Phillips) discloses a catalyst based on a chromium source, a 2,5-dimethylpyrrole ligand and an alkyl aluminium activator for use in the trimerization of ethylene to 1-hexene.

Chem. Commun., 2002, 8, 858-859 (BP), discloses chromium complexes of ligands of the type $Ar_2PN(Me)PAr_2$ (Ar=ortho-methoxy-substituted aryl group) as catalysts for the trimerization of ethylene.

U.S. 2003/0166456, which is hereby incorporated by reference in its entirety, (BP) discloses a catalyst for the trimerization of olefins comprising a source of chromium, molybdenum or tungsten, a ligand containing at least one phosphorus, arsenic or antimony atom bound to at least one hydrocarbyl or heterohydrocarbyl group having a polar substituent, but excluding the case where all such polar substituents are phosphane, arsane or stibane groups, and optionally an activator. The ligand used in most of the examples is $(2\text{-methoxyphenyl})_2PN(Me)P(2\text{-methoxyphenyl})_2$.

Although the catalysts disclosed in the BP documents mentioned above have good selectivity for 1-hexene within the $C_6$ fraction, a relatively high level of by-product formation (e.g. decenes) is observed. It would therefore be desirable to provide a catalyst for the trimerization of olefinic monomers, especially for the trimerization of ethylene to 1-hexene, which reduces by-product formation (e.g. decenes) while maintaining selectivity for 1-hexene.

It has now been surprisingly found that the catalyst compositions and processes of the present invention provide an efficient route for the selective production of 1-hexene from ethylene while reducing the level of by-product formation, especially $C_{10}$.

SUMMARY OF THE INVENTION

According to one aspect of the present invention there is provided a catalyst composition suitable for the trimerization of olefinic monomers, wherein the catalyst composition comprises:
  a) a source of chromium, molybdenum or tungsten;
  b) a ligand of general formula (I);

$$(R^1)(R^2)P\text{---}X\text{---}P(R^3)(R^4) \tag{I}$$

wherein:
  X is a bivalent organic bridging group comprising from 1 to 10 carbon atoms in the bridge;
  $R^1$ and $R^3$ are independently selected from hydrocarbyl, substituted hydrocarbyl, heterohydrocarbyl and substituted heterohydrocarbyl groups, with the proviso that when $R^1$ and $R^3$ are cycloaromatic groups they do not contain a polar substituent at any of the ortho-positions;
  $R^2$ and $R^4$ are independently selected from optionally substituted cycloaromatic groups, each $R^2$ and $R^4$ bearing a polar substituent on at least one of the ortho-positions; and
  c) a cocatalyst.

According to a further aspect of the present invention, there is provided a process for the trimerization of olefinic monomers, wherein the process comprises contacting at least one olefinic monomer under trimerization reaction conditions with said catalyst composition.

The catalyst compositions of the present invention are particularly suitable for the trimerization of olefinic monomers, especially for the trimerization of ethylene to 1-hexene. The catalyst compositions and process of the present invention surprisingly produce substantially lower concentrations of olefinic by-products (e.g. decenes, predominantly 1-decene which is produced by the addition of two ethylene monomers to the 1-hexene product) while maintaining a high selectivity for 1-hexene. In addition, the catalyst compositions of the present invention display improved activity/decay rate profiles compared to the Cr(III) (2-methoxyphenyl) $2PN(Me)P(2\text{-methoxyphenyl})_2$ catalysts disclosed in US 2003/0166456, which is hereby incorporated by reference in its entirety, mentioned above. In particular, the catalyst compositions of the present invention show good initial activity but decay less quickly than the Cr(III)(2-methoxyphenyl)$_2$PN (Me) P(2-methoxyphenyl)$_2$ catalysts.

DETAILED DESCRIPTION OF THE INVENTION

As used herein, the term "trimerization" means the catalytic trimerization of an olefinic monomer to give a product composition enriched in the compound derived from the reaction of three of said olefinic monomers. The term trimerization includes the cases wherein all the olefinic monomers in the feed stream are identical as well as the cases wherein the feed stream contains two or more different olefinic monomers.

In particular, the term "trimerization" when used in relation to the trimerization of ethylene means the trimerization of ethylene to form a $C_6$ alkene, especially 1-hexene.

The term "trimerization selectivity" when used in relation to the trimerization of ethylene to 1-hexene means the amount of C6 fraction formed within the product composition.

The term "1-hexene selectivity" when used in relation to the trimerization of ethylene to 1-hexene means the amount of 1-hexene formed within the C6 fraction of the product composition. The overall yield of 1-hexene in the trimerization of ethylene is the product of the "trimerization selectivity" multiplied by the "1-hexene selectivity".

The catalyst composition of the present invention comprises:
 a) a source of chromium, molybdenum or tungsten;
 b) a ligand; and
 c) a cocatalyst.

Each of these three essential components is described in detail below.

The source of chromium, molybdenum or tungsten, component (a), for the catalyst composition can include simple inorganic and organic salts of chromium, molybdenum or tungsten. Examples of simple inorganic and organic salts are halides, acetylacetonates, carboxylates, oxides, nitrates, sulfates and the like. Further sources of chromium, molybdenum or tungsten can also include co-ordination and organometallic complexes, for example chromium trichloride tetrahydrofuran complex, (benzene)tricarbonylchromium, chromium hexacarbonyl, and the like.

The source of chromium, molybdenum or tungsten can also include a mixture of simple inorganic salts, simple organic salts, co-ordination complexes and organometallic complexes.

In a preferred embodiment herein, component (a) is a source of chromium, particularly chromium (III).

Preferred sources of chromium for use herein are simple inorganic and organic salts of chromium. A more preferred source of chromium for use herein are the halide salts of chromium, such as chromium chloride, chromium bromide, chromium fluoride, and chromium iodide. A particularly preferred source of chromium for use herein is chromium chloride, $CrCl_3$.

The ligand of the catalyst composition of the present invention, component (b), is of the general formula (I);

$(R^1)(R^2)P—X—P(R^3)(R^4)$  (I)

wherein:

X is a bivalent organic bridging group comprising from 1 to 10 carbon atoms in the bridge;

$R^1$ and $R^3$ are independently selected from hydrocarbyl, substituted hydrocarbyl, heterohydrocarbyl and substituted heterohydrocarbyl groups with the proviso that when $R^1$ and $R^3$ are cycloaromatic groups they do not contain a polar substituent at any of the ortho-positions;

$R^2$ and $R^4$ are independently selected from optionally substituted cycloaromatic groups, each $R^2$ and $R^4$ bearing a polar substituent on at least one of the ortho-positions.

In the general formula (I), X represents a bivalent organic bridging group, comprising from 1 to 10, preferably from 2 to 6, more preferably from 2 to 4 and especially from 2 to 3 carbon atoms in the bridge. A preferred embodiment has 2 carbon atoms in the bridge.

By "in the bridge" is understood to be the shortest connection between the two phosphorus atoms.

Suitable bridging groups include substituted and unsubstituted alkylene groups. The alkylene groups can optionally contain one or more heteroatoms in the bridge, such as N, S, Si or O. Preferably, the alkylene group contains only carbon atoms in the bridge.

The alkylene groups can be substituted with one or more substituents. The substituents can be attached to any part of the connection.

The substituents on the alkylene bridging group can contain carbon atoms and/or heteroatoms. Suitable substituents include hydrocarbyl groups which may be straight-chain or branched, saturated or unsaturated, aromatic or non-aromatic. The hydrocarbyl substituents may optionally contain heteroatoms such as Si, S, N or O. Suitable aromatic hydrocarbyl substituents include cycloaromatic groups, preferably having from 5 to 10 carbon atoms in the ring, such as phenyl and $C_1$-$C_4$ alkyl phenyl groups. Suitable non-aromatic hydrocarbyl substituents include linear or branched alkyl or cycloalkyl groups, preferably having from 1 to 10 carbon atoms, more preferably 1 to 4 carbon atoms.

Other suitable substituents of the alkylene bridging group include halides such as chloride, bromide and iodide, thiol, —OH, $A^1$-O—, —S-$A^1$, —CO-$A^1$, —$NH_2$, —NHA , —$NA^1A^2$, —CO—$NA^1A^2$, —$PO_4$, —$NO_2$, —CO, —$SO_2$, in which $A^1$ and $A^2$, independently, are non-aromatic groups preferably having from 1 to 10 carbon atoms, more preferably 1 to 4 carbon atoms, eg. methyl, ethyl, propyl and isopropyl.

When the alkylene bridging group is substituted, preferred substituents are hydrocarbyl groups. Particularly preferred hydrocarbyl substituents are $C_1$-$C_4$ alkyl groups, preferably methyl, ethyl, propyl, isopropyl, butyl, isobutyl, most preferably methyl.

Examples of non-substituted alkylene bridging groups include methylene, ethylene and trimethylene groups. Examples of substituted alkylene bridging groups include 2,2-dimethyl-trimethylene, 2,2-diethyl-trimethylene, 2,2-dimethyl-tetramethylene, 2-methyl, 2-hydroxymethyl-trimethylene and 2,2-di-hydroxymethyl-trimethylene.

Particularly preferred organic bridging groups for use herein are unsubstituted alkylene bridging groups. An especially preferred organic bridging group is ethylene, that is, —$CH_2$—$CH_2$—.

Other suitable bridging groups are those where the connection forms part of a non-aromatic or aromatic ring structure. Such bridging groups comprise one or more substituted or unsubstituted, saturated or unsaturated non-aromatic ring structures and/or one or more substituted or unsubstituted cycloaromatic (including heteroaromatic) ring structures. The non-aromatic ring structure may be interrupted by one or more heteroatoms such as N, S, Si or O. Preferably such a bridging group still contains only 2 to 6 carbon atoms in the bridge.

Suitable non-aromatic ring structures include cyclopentane, cyclohexane, cyclohexene, cyclopentene, 3,4-furan and 3,4-thiophene.

Suitable aromatic ring structures include phenylene, in particular 1,2-phenylenes, and naphthylene, in particular 1,8- or 1,2-naphthylenes.

The ring structures may be substituted with any kind of substituent, including heteroatoms, alkyl groups, cycloalkyl groups and cycloaromatic groups. Suitable substituents include those mentioned above in relation to alkylene bridging groups. It is preferred that the two phosphorus atoms are attached to the ring system at adjacent positions, i.e. positions 1 and 2.

$R^1$ and $R^3$ are independently selected from, hydrocarbyl, substituted hydrocarbyl, heterohydrocarbyl and substituted heterohydrocarbyl groups, with the proviso that when $R^1$ and $R^3$ are cycloaromatic groups they do not contain a polar substituent at any of the ortho-positions.

The term "hydrocarbyl" as used herein refers to a group only containing carbon and hydrogen atoms. The hydrocarbyl group may be a saturated or unsaturated, linear or branched alkyl, a non-aromatic ring or a cycloaromatic ring. Preferred hydrocarbyl groups for use herein are those containing from 1 to 20 carbon atoms.

The term "substituted hydrocarbyl" as used herein refers to hydrocarbyl groups which contain one or more inert heteroatom containing functional groups. By "inert heteroatom containing functional groups" is meant that the functional groups do not interfere to any substantial degree with the trimerization process.

The term "heterohydrocarbyl" as used herein refers to a hydrocarbyl group wherein one or more of the carbon atoms is replaced by a heteroatom, such as S, N or O. The term "substituted heterohydrocarbyl" as used herein refers to heterohydrocarbyl groups which contain one or more inert heteroatom containing functional groups.

The term "cycloaromatic" as used herein, refers to a monocyclic or polycyclic, aromatic or heteroaromatic ring having from 5 to 14 ring atoms, optionally containing from 1 to 3 heteroatoms selected from N, O and S. Preferably, the cycloaromatic groups are monocyclic or polycyclic aromatic rings, such as cyclopentadienyl, phenyl, naphthyl or anthracenyl. Even more preferred cycloaromatic groups are monocyclic or polycyclic aromatic rings having from 5 to 10 ring atoms. Especially preferred cycloaromatic groups are monocyclic aromatic rings containing from 5 to 6 carbon atoms, such as phenyl and cyclopentadienyl, and a most prefered cycloaromatic group is a phenyl group.

The term "substituted cycloaromatic" as used herein means that the cycloaromatic group may be substituted with one or more substituents. Suitable substituents include those mentioned above in relation to the alkylene bridging group.

In one preferred embodiment, $R^1$ and $R^3$ are independently selected from substituted or unsubstituted cycloaromatic groups which do not contain a polar substituent at any of the ortho-positions. In an even more preferred embodiment, $R^1$ and $R^3$ are independently selected from optionally substituted phenyl groups which do not contain a polar substituent at any of the ortho-positions. In an especially preferred embodiment, $R^1$ and $R^3$ are unsubstituted phenyl groups.

It is preferred that the $R^1$ and $R^3$ groups are the same.

$R^2$ and $R^4$ are independently selected from optionally substituted cycloaromatic groups, each $R^2$ and $R^4$ group bearing a polar substituent on at least one of the ortho-positions. For the avoidance of doubt, the phrase "each $R^2$ and $R^4$ bearing a polar substituent on at least one of the ortho-positions" means that, in the same ligand, $R^2$ is substituted with a polar substituent on one or both of its' ortho positions and $R^4$ is substituted with a polar substituent on one or both of its' ortho-positions.

The term "optionally substituted" in relation to $R^2$ and $R^4$ means that, in addition to the polar substituent on at least one of the ortho-positions, the $R^2$ and $R^4$ groups may contain one or more substituents. Suitable substituents include those mentioned in relation to the alkylene bridging group.

Preferably, $R^2$ and $R^4$ are independently selected from optionally substituted cycloaromatic groups having from 5 to 14 ring atoms, preferably from 5 to 10 ring atoms, wherein each $R^2$ and $R^4$ bears a polar substituent on at least one of the ortho-positions.

In one preferred embodiment, $R^2$ and $R^4$ are independently selected from optionally substituted phenyl groups, wherein each $R^2$ and $R^4$ bears a polar substituent on at least one of the ortho-positions.

Preferably, each of $R^2$ and $R^4$ bears a polar substituent on one of the two ortho-positions.

As used herein, the term "polar substituents" means a substituent which incorporates an electronegative centre.

Suitable polar substituents for use herein include but are not necessarily limited to, optionally branched $C_1$-$C_{20}$ alkoxy groups, i.e. hydrocarbyl groups connected to the $R^2$ and $R^4$ cycloaromatic ring through an oxygen bridging atom; optionally substituted $C_5$-$C_{14}$ aryloxy groups, i.e. optionally substituted cycloaromatic groups connected to the $R^2$ and $R^4$ cycloaromatic ring through an oxygen bridging atom; optionally branched $C_1$-$C_{20}$ alkyl($C_1$-$C_{20}$)alkoxy groups, i.e. $C_1$-$C_{20}$ hydrocarbyl groups bearing a $C_1$-$C_{20}$ alkoxy group; hydroxyl; amino; (di-)$C_1$-$C_6$alkylamino; nitro; $C_1$-$C_6$alkylsulphanyl; $C_1$-$C_6$alkylthio$C_1$-$C_6$alkyl groups; and tosyl groups.

Examples of suitable polar substituents include methoxy, ethoxy, isopropoxy, phenoxy, pentafluorophenoxy, trimethylsiloxy, dimethylamino, methylsulphanyl, tosyl, methoxymethyl, methylthiomethyl, 1,3-oxazolyl, hydroxyl, amino, sulphate, nitro and the like.

Preferably, the polar substituents on $R^2$ and $R^4$ are independently selected from optionally branched $C_1$-$C_{20}$ alkoxy groups, optionally substituted $C_5$-$C_{14}$ aryloxy groups, and optionally branched $C_1$-$C_{20}$ alkyl($C_1$-$C_{20}$)alkoxy groups. More preferably, the polar substituents on $R^2$ and $R^4$ are independently selected from optionally branched $C_1$-$C_{20}$ alkoxy groups, especially optionally branched $C_1$-$C_6$ alkoxy groups such as, for example, methoxy, ethoxy or isopropoxy. A particularly preferred polar substituent on $R^2$ and $R^4$ is methoxy.

It is preferred that the $R^2$ and $R^4$ groups are the same and bear the same number and type of polar substituent(s). It is particularly preferred that $R^2$ bears only one polar substituent on one of its' two ortho-positions and that $R^4$ bears only one polar substituent on one of its' two ortho-positions.

The ligands according to formula (I) can be prepared using procedures known to one skilled in the art or disclosed in published literature. Examples of such compounds are:

(2-methoxyphenyl)(phenyl)PCH$_2$CH$_2$P(2-methoxyphenyl)(phenyl)

(2-methoxyphenyl)(phenyl)PCH$_2$P(2-methoxyphenyl)(phenyl)

(2-methoxyphenyl)(phenyl)PCH$_2$CH$_2$CH$_2$P(2-methoxyphenyl)(phenyl)

(2-ethoxyphenyl)(phenyl)PCH$_2$CH$_2$P(2-ethoxyphenyl)(phenyl)

(2-ethoxyphenyl)(phenyl)PCH$_2$P(2-ethoxyphenyl)(phenyl)

(2-ethoxyphenyl)(phenyl)PCH$_2$CH$_2$CH$_2$P(2-ethoxyphenyl)(phenyl)

(2-isopropoxyphenyl)(phenyl)PCH$_2$CH$_2$P(2-isopropoxyphenyl)(phenyl)

(2-isopropoxyphenyl)(phenyl)PCH$_2$P(2-isopropoxyphenyl)(phenyl)

(2-isopropoxyphenyl)(phenyl)PCH$_2$CH$_2$CH$_2$P(2-isopropoxyphenyl)(phenyl)

A particularly preferred ligand for use herein is (2-methoxyphenyl)(phenyl)PCH$_2$CH$_2$P(2-methoxyphenyl)(phenyl).

The source of chromium, molybdenum or tungsten, component (a), and the ligand, component (b), can be present in the catalyst composition of the present invention in a molar ratio in the range from about 10000:1 to about 1:10000, preferably from about 100:1 to about 1:100, more preferably from about 10:1 to about 1:10. Most preferably, components (a) and (b) are present in a ratio in the range from about 3:1 to about 1:3. Generally the amounts of (a) and (b) are approximately equal, i.e. a ratio in the range from about 1.5:1 to about 1:1.5.

The cocatalyst, component (c), may in principle be any compound or mixture of compounds that generates an active catalyst with the source of chromium, molybdenum or tungsten, component (a), and the ligand, component (b).

Compounds which are suitable for use as a cocatalyst include organoaluminium compounds, organoboron compounds and inorganic acids and salts, such as tetrafluoroboric acid etherate, silver tetrafluoroborate, sodium hexafluoroantimonate and the like.

Particularly preferred cocatalysts are organoaluminium compounds. Suitable organoaluminium compounds for use herein are those having the formula $AlR_3$, wherein each R group is independently selected from $C_1$-$C_{30}$ alkyl, oxygen or halides, or compounds such as $LiAlH_4$ and the like. Non-limiting examples of suitable organoaluminium compounds include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride and alumoxanes. Mixtures of organoaluminium compounds are also suitable for use herein.

In a preferred embodiment herein, the cocatalyst is an alumoxane cocatalyst. These alumoxane cocatalysts may comprise any alumoxane compound or a mixture of alumoxane compounds. Alumoxanes may be prepared by the controlled addition of water to an alkylaluminium compound, such as those mentioned above, or are available commercially. In this context it should be noted that the term "afumoxane" as used within this specification includes commercially available alumoxanes which may contain a proportion, typically about 10% wt., but optionally up to about 50% wt., of the corresponding trialkylaluminium. For instance, commercial methylalumoxane (MAO) usually contains approximately 10% wt. trimethylaluminium (TMA), whilst modified methylalumoxane (MMAO) contains both TMA and tri-isobutylaluminium (TIBA). The molar ratio of water to aluminium compound in the preparation of the alumoxanes is preferably in the range from 0.01:1 to about 2.0:1, more preferably from about 0.02:1 to about 1.2:1, even more preferably from about 0.4:1 to about 1:1, especially about 0.5:1. These alumoxane compounds may be linear, cyclic cages or mixtures thereof. Preferred alumoxanes are linear alumoxanes of the formula $R^5(R^6AlO)_n$ wherein n is a number from about 2 to 50 and $R^5$ and $R^6$ are $C_1$ to $C_6$ alkyl groups. The most preferred alumoxanes are methylalumoxane (MAO) or modified methylalumoxane (MMAO) which contains both TMA and TIBA.

Other suitable co-catalysts include those disclosed in US 2003/0166456 which is hereby incorporated by reference in its entirety.

The quantity of cocatalyst used in the present invention is typically enough to provide a ratio in the range from about 0.1 to about 20,000, preferably from about 1 to about 2000, aluminium or boron atoms per atom of chromium, molybdenum or tungsten.

The catalyst composition of the present invention may also be mixed with at least one other trimerization catalyst.

The three essential catalyst components, (a), (b) and (c), may be added together simultaneously or sequentially in any order so as to provide an active catalyst. The three essential catalyst components may be contacted in the presence of any suitable solvent. Suitable solvents are known to those skilled in the art. Examples of suitable solvents are those disclosed in US 2003/0166456 which is hereby incorporated by reference in its entirety.

The catalyst composition of the present invention may be prepared either in the presence (i.e. "in-situ") or absence of the olefinic monomer. The three essential components of the catalyst composition may be combined fully in the absence of the olefinic monomer, or the olefinic monomer may be included prior to contacting the catalyst components, simultaneously with the catalyst components or at any point in the process of contacting the catalyst components.

The three essential catalyst components may be unsupported or supported on a support material. Examples of suitable support materials can be found in US 2003/0166456 which is hereby incorporated by reference in its entirety.

The olefinic monomers suitable for use in the trimerization process of the present invention can be any olefinic monomers which can be converted into a trimer. Suitable olefinic monomers include, but are not necessarily limited to, ethylene, propylene, optionally branched $C_4$-$C_{20}$ α-olefins, optionally branched $C_4$-$C_{20}$ internal olefins, optionally branched $C_4$-$C_{20}$ vinylidene olefins, optionally branched $C_4$-$C_{20}$ cyclic olefins and optionally branched $C_4$-$C_{20}$ dienes, as well as optionally branched $C_4$-$C_{20}$ functionalized olefins. Examples of suitable olefinic monomers include, but are not necessarily limited to, ethylene, propylene, 1-butene, 1-pentene, 1-hexene, 4-methylpent-1-ene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, styrene, 2-butene, 1-ethyl-1-hexene, cyclohexene, norbornene and the like.

Mixtures of olefinic monomers can also be used in the process of the present invention.

Preferred olefinic monomers for use in the trimerization process of the present invention are propylene and ethylene. Especially preferred is ethylene.

The catalyst compositions and process of the present invention are particularly useful for the trimerization of ethylene to 1-hexene.

The trimerization process of the present invention can be performed under a range of process conditions known to one skilled in the art or disclosed in published literature such as, for example, those disclosed in US 2003/0166456 which is hereby incorporated by reference in its entirety.

The trimerization reaction can be performed in solution phase, slurry phase, gas phase or bulk phase.

When the trimerization is performed in solution or slurry phase, a diluent or solvent which is substantially inert under trimerization conditions may be employed. Suitable diluents or solvents are aliphatic and aromatic hydrocarbons, halogenated hydrocarbons and olefins which are substantially inert under trimerization conditions may be employed, such as those disclosed in US 2003/0166456 which is hereby incorporated by reference in its entirety.

The trimerization process of the present invention may be carried out under a wide range of process conditions which are well known to a person skilled in the art. Typically, the temperature will be in the range from about −100° C. to about 200° C., preferably from about 0° C. to about 150° C., and more preferably from about 25° C., to about 100° C. Typically, the pressure will be in the range from about 0 to about 100 barg, preferably from about 1 to about 50 barg.

The trimerization process of the present invention may be performed in any one of a number of suitable reactors which are well known to one skilled in the art. Typically the trimerization process of the present invention is carried out in a batch, semi-batch or continuous mode.

Separation of the product, reactant and catalyst can be performed by any technique known to one skilled in the art, such as distillation, filtration, centrifugation, liquid/liquid separation, extraction, etc.

Further details regarding suitable trimerization reaction conditions, including further details on reactors, solvents, separation techniques, and the like, can be found in US 2003/0166456 which is hereby incorporated by reference in its entirety.

The use of the catalyst composition and process of the present invention for the catalytic trimerization of ethylene to 1-hexene provides a very high selectivity for 1-hexene over all the other products formed in the reaction.

The catalyst composition of the present invention provides an overall yield of 1-hexene from the trimerization of ethylene that is greater than the overall yield of 1-hexene from the trimerization of ethylene using an equivalent catalyst composition, which does not contain a ligand of the type of the present invention (but which, for example, contains a ligand of formula —PN(CH$_3$)P—, as disclosed in WO 02/04119), under identical reaction conditions. Preferably, the catalyst composition of the present invention provides overall yield of 1-hexene from the trimerization of ethylene that is up to 35% greater than the overall yield of 1-hexene from the trimerization of ethylene using an equivalent catalyst composition, which does not contain a ligand of the type of the present invention, under identical reaction conditions. More preferably, the catalyst composition of the present invention will provide an overall yield of 1-hexene from the trimerization of ethylene that is at least 5% greater than the overall yield of 1-hexene from the trimerization of ethylene using an equivalent catalyst composition, which does not contain a ligand of the type of the present invention, under identical reaction conditions.

The amount of 1-hexene produced from the trimerization of ethylene using the catalyst composition of the present invention is at least about 80%, by weight, preferably at least about 85%, by weight, more preferably at least about 90%, by weight, and especially at least about 95% by weight, of the final product composition.

The trimerization selectivity (i.e. the amount of C6 fraction in the product composition) for the trimerization of ethylene using the catalyst composition of the present invention is at least about 80% wt. Preferably, the trimerization selectivity for the trimerization of ethylene using the catalyst composition of the present invention is greater than the trimerization selectivity for the production of C$_6$ compounds from the trimerization of ethylene using an equivalent catalyst composition, which does not contain a ligand of the type of the present invention (but which, for example, contains a ligand of formula —PN(CH$_3$)P—, as disclosed in WO 02/04119), under identical reaction conditions. Preferably, the trimerization selectivity for the trimerization of ethylene using the catalyst composition of the present invention is up to about 40% greater than the trimerization selectivity for the trimerization of ethylene using an equivalent catalyst composition, which does not contain a ligand of the type of the present invention,. under identical reaction conditions. It is also preferred that the catalyst composition of the present invention has a trimerization selectivity for the trimerization of ethylene that is at least 5% greater than the trimerization selectivity for the trimerization of ethylene using an equivalent catalyst composition, which does not contain a ligand of the type of the present invention, under identical reaction conditions.

The production of C$_{10}$ by-product compounds in the trimerization of ethylene using the catalyst composition of the present invention is preferably at most about 60% the level of C$_{10}$ by-product compounds produced in the trimerization of ethylene using an equivalent catalyst composition, which does not contain a ligand of the type of the present invention (e.g. Cr(III)(2-methoxyphenyl)$_2$PN(CH$_3$)P(2-methoxyphenyl) 2), under identical reaction conditions. More preferably, the production of C$_{10}$ by-product compounds in the trimerization of ethylene using the catalyst composition of the present invention is at most about 50% of the level of C$_{10}$ by-product compounds produced in the trimerization of ethylene using an equivalent catalyst composition, which does not contain a ligand of the type of the present invention, under identical reaction conditions. Even more preferably, the production of C$_{10}$ by-product compounds in the trimerization of ethylene using the catalyst composition of the present invention is at most about 30% of the level of C$_{10}$ by-product compounds produced in the trimerization of ethylene using an equivalent catalyst composition, which does not contain a ligand of the type of the present invention, under identical reaction conditions. In an especially preferred embodiment, the production of C$_{10}$ by-product compounds in the trimerization of ethylene using the catalyst composition of the present invention is at most about 20% of the level of C$_{10}$ by-product compounds produced in the trimerization of ethylene using an equivalent catalyst composition, which does not contain a ligand of the type of the present invention, under identical reaction conditions.

The catalyst compositions and process of the present invention are illustrated by the following non-limiting examples.

EXAMPLES

A number of compositions (Compositions 1, 2 and 3) containing a ligand component and a chromium source were prepared for use in the trimerization reactions described below.

Composition 1

(2-methoxyphenyl)(phenyl) PCH$_2$CH$_2$P(2-methoxyphenyl)(phenyl) in a 1:1 molar ratio with CrCl$_3$.

The (2-methoxyphenyl)(phenyl) PCH$_2$CH$_2$P(2-methoxyphenyl)(phenyl) ligand is prepared according to the following method.

Under a nitrogen atmosphere, to a solution of o-bromoanisole (0.54 mol) in pentane (150 ml), n-butyllithium solution (337 ml, 0.54 mol) is added slowly with constant stirring. The mixture is stirred overnight, after which, the stirring is stopped and the suspension is allowed to settle out. The liquor is decanted and the solid residue of o-anisyllithium is washed with pentane and dried under high vacuum.

0.20 mol of o-anisyllithium is dissolved in diethyl ether (400 ml) and cooled to −20° C. Slowly added under constant stirring to this solution is 0.1 mol ethyl phenylphosphinate. The solution is then allowed to reach 25° C., after which the solution is then refluxed for 2 hours. The solution is then allowed to cool, after which 0.1 M hydrochloric acid is added (150 ml). The product is then extracted with three 50 ml portions of dichloromethane. The combined organic layers are then combined and dried using magnesium sulfate. The solvents are then removed to give an oil and then excess anisole is removed by warming (70° C.) under vacuum. The last traces of anisole are removed by washing the resultant white solid ((2-methoxyphenyl)(phenyl)phosphine oxide) with diethyl ether, followed by crystallisation from chloroform/diethyl ether.

40 mmol of the (2-methoxyphenyl)(phenyl)phosphine oxide is added to tetrahydrofuran (600 ml) to which n-butyllithium solution (25 ml, 40 mmol) is added at 0° C. The orange homogeneous solution of the lithium salt formed is then allowed to stir for 1 hour at room temperature and then cooled to 0° C. To this solution 1,2-ethanediyl bis-tosylate (20 mmol) is added. The temperature of the solution is then allowed to increase to room temperature. A slurry is formed as the solution is heated and refluxed overnight. The mixture is then cooled and the reaction is quenched by the addition of water (150 ml). The product is then extracted into dichloromethane (3×100 ml) followed by drying with magnesium sulfate. Concentration of the solution affords the 1,2-ethandiyl(2-methoxyphenyl)(phenyl)phosphine oxide product as a white solid.

To a 2 mmol solution of the 1,2-ethandiyl(2-methoxyphenyl)(phenyl)phosphine oxide product in tetrahydrofuran (250 ml), aluminium hydride ($AlH_3.1/3(C_2H_5)_2O$, 20 mmol) is added dropwise. The solution is then refluxed until complete (generally overnight), after which, the reaction is quenched by the addition of methanol (10 ml), followed by the filtration of the aluminium salt precipitate. The filtrate is then concentrated. Addition of methanol affords the crystalline (2-methoxyphenyl) (phenyl)$PCH_2CH_2P$(2-methoxyphenyl)(phenyl) product.

Composition 2 (Comparative)

(2-methoxyphenyl)$_2$PN($CH_3$)P(2-methoxyphenyl)$_2$ in a 1:1 molar ratio with $CrCl_3$.

The (2-methoxyphenyl)$_2$PN($CH_3$)P(2-methoxyphenyl)$_2$ ligand was prepared by first forming a solution of 1.59 g (5 mmol) (2-methoxyphenyl)$_2$PNEt$_2$ in 20 ml diethyl ether. To this solution 10 ml of a 1 M HCl solution in diethyl ether (10-mmol HCl) was added under an inert atmosphere at room temperature. The suspension thus formed was stirred overnight. The diethyl ether was removed from the product under vacuum and 20 ml of dry toluene was added. The resulting solution was filtered and the toluene was removed from the filtrate under vacuum to yield a white solid (2-methoxyphenyl)$_2$PCl product.

A solution of 0.51 g (5 mmol) of triethylamine in 20 ml of dry dichloromethane was added to the (2-methoxyphenyl)$_2$PCl product. To the resulting mixture, 1.25 ml of a 2 M H$_2$NMe solution in THF (2.5 mmol) was added and allowed to stir overnight. The solvents were removed from the resulting solution in vacuo and 20 ml of dry toluene was added. The mixture was then filtered. The toluene was removed from the filtrate under vacuum, and 10 ml of methanol was added. The suspension was filtered once more, and the solid white (2-methoxyphenyl$_2$PN(CH$_3$)P(2-methoxyphenyl)$_2$ product was isolated.

Composition 3 (Comparative)

(2-methoxyphenyl) (phenyl)PN(CH$_3$)P(2-methoxyphenyl)(phenyl) in a 1:1 molar ratio with CrCl$_3$.

The (2-methoxyphenyl)(phenyl)PN(CH$_3$)P(2-methoxyphenyl)(phenyl) ligand was prepared by first forming a suspension of 0.42 g lithium (60 mmol) in 80 ml of THF, to which was added 9.66 g of (2-methoxyphenyl)$_2$P(phenyl) (30 mmol) at 0° C. under an argon atmosphere. The mixture was stirred for 4 hours, after which time a 5 ml aliquot of methanol was added. 60 ml of toluene was added to the mixture, after which the solution was extracted with two 40 ml portions of water. The extracted toluene solution was then concentrated to a volume of approximately 20 ml, which resulted in formation of a suspension. The concentrated toluene solution was filtered, and 4.6 g of C$_2$Cl$_6$ (24 mmol) was added to the toluene filtrate, which was then stirred for 2 hours at 90° C. The HCl gas which evolved from the reaction was "trapped" in an alkali bath. The mixture was then cooled to room temperature and purged with nitrogen to remove all of the remaining HCl present in the solution.

At room temperature, a 5 ml aliquot of triethylamine was added to the concentrated toluene solution and left for a few minutes, after which 6 ml of 2 M H$_2$NMe (12 mmol) was added a few drops at a time. The suspension was filtered and washed with 20 ml of toluene. The toluene filtrate and the toluene wash fraction were combined. The combined toluene fractions were evaporated to dryness and 30 ml of methanol was added. The methanol solution was left overnight at −35° C. wherein a white (2-methoxyphenyl)(phenyl)PN(CH$_3$)P(2-methoxyphenyl)(phenyl) precipitate was formed in the solution. The precipitated ligand was then isolated.

The precipitated ligand consisted of two isomers, a racemic isomer (the RR and/or the SS enantiomers of the ligand) and a meso isomer (the RS enantiomer of the ligand). The proportions of these two isomers were determined by $^{31}$p NMR with peaks at 63.18 and 64.8 ppm corresponding to the two different isomers respectively. Two samples of (2-methoxyphenyl)(phenyl)PN(CH$_3$)P(2-methoxyphenyl) (phenyl) were used in the examples. These two samples consisted of mixtures of both the racemic and the meso isomers having weight ratios of 57/43 and 92/8 respectively.

Endeavor Procedure

Examples 1-8 were performed using the following set-up and procedure. The 'Endeavor' (trademark of Argonaut Technologies, Inc.) is a multi reactor set-up containing eight glass lined 15 ml reactors, used for reactions performed under pressure (up to 30 bar). The present reactions were performed on a 5 to 10 ml volume scale.

The procedure for the trimerization of ethylene to 1-hexene was performed as follows.

The reactors were purged three times with ethylene at 100° C. and a pressure of 30 bar. The reactors were then left to cool to room temperature whilst maintaining a pressure of 20-30 bar of ethylene. The ethylene inlet valve was closed and the reactors were left overnight. Also by monitoring the ethylene pressure inside the reactors overnight the reactors were tested for leaks. The reactors were then ready for the reactions the following day.

A catalyst premix solution was prepared for the appropriate catalyst which was to be used. The catalyst premix solution was prepared by weighing 10 pmol of Composition 1, 2 or 3, adding 7.4 g of dry toluene and adding 1.26 g (3 mmol) of a solution of modified methylalumoxane (referred to from hereon as MMAO) solution (6.4 wt. % Al in heptane, supplied by Witco Co.). Thus, the premix solution prepared (10 ml) contained a total of 10 pmol of Cr and 3 mmol of Al (1 mM Cr, 0.3 M Al), and therefore an Al:Cr ratio of 300:1. The premix solution was allowed to stir overnight under a nitrogen atmosphere at room temperature and atmospheric pressure.

A 0.2 M MMAO scavenger solution (5 ml) was prepared by adding a 1 mmol (422 mg) quantity of MMAO solution (6.4 wt. % Al in heptane) to-3.9 g of toluene.

The reactors were then charged with an appropriate amount of the 0.2 M MMAO scavenger solution and 2.5 ml of additional toluene. The reactors were then heated to 80° C. and pressurised with ethylene to the desired reaction pressure. To start the trimerization reaction, an aliquot of the premix solution was injected into the reactors. A further 0.5 ml of toluene was then injected to purge the injection line of any remaining catalyst premix solution.

The reaction was stopped either when the maximum uptake of ethylene was reached or after a set time by closing off the ethylene inlet valve, cooling to room temperature, depressurising and opening the reactor. The term "stopped when the maximum uptake of ethylene was reached" as used herein means, the amount of ethylene consumed in the reaction corresponds to the amount of ethylene required to produce the specific desired volume of 1-hexene. For example, if a 5 ml final volume of 1-hexene is desired (0.04 moles), the number of moles of ethylene required to produce the 5 ml final volume of 1-hexene would be 0.12 moles, thus the supply of ethylene to the reactor would cease once 0.12 moles of ethylene had been supplied. This is important as the volume of the reactors in the 'Endeavor' was approximately 15 ml, and as such the desired final volume of product and any remaining starting materials was less than 15 ml. Typically a 5-10 ml final volume was desired.

The product mixture was collected and weighed. A weighed amount was analysed using Gas Chromatography (GC) (50 m CPSIL 5 CB y 0.25 column, helium carrier gas, FID detector) with a known amount of hexylbenzene internal standard.

Example 1

In this experiment, the reactor containing 0.5 ml of the 0.2 M MMAO scavenger solution and heated to 80° C., was pressurised to 8 bar with ethylene. A 0.5 ml aliquot of the catalyst premix solution, containing Composition 1, was injected into the reactor to start the reaction (Al:Cr ratio of 500:1). The reaction was stopped when the maximum uptake of ethylene was reached (161 minutes).

The product mixture was analysed by GC. The results can be found in Table 1.

Example 2

In this experiment, the reactor containing 0.5 ml of the 0.2 M MMAO scavenger solution and heated to 80° C., was pressurised to 20 bar with ethylene. A 0.5 ml aliquot of the catalyst premix solution, containing Composition 1, was injected into the reactor to start the reaction (Al:Cr ratio of 500:1). The reaction was stopped when the maximum uptake of ethylene was reached (96 minutes).

The product mixture was analysed by GC. The results can be found in Table 1.

Example 3

In this experiment, the reactor containing 0.5 ml of the 0.2 M MMAO scavenger solution and heated to 80° C., was pressurised to 8 bar with ethylene. A 0.5 ml aliquot of the catalyst premix solution, containing Composition 1, was injected into the reactor to start the reaction (Al:Cr ratio of 500:1). The reaction was stopped after 1 hour.

The product mixture was analysed by GC. The results can be found in Table 1.

Example 4

In this experiment, the reactor containing 0.35 ml of the 0.2 M MMAO scavenger solution and heated to 80° C., was pressurised to 15 bar with ethylene. A 0.35 ml aliquot of the catalyst premix solution, containing Composition 1, was injected into the reactor to start the reaction (Al:Cr ratio of 500:1). The reaction was stopped after 1 hour.

The product mixture was analysed by GC. The results can be found in Table 1.

Example 5 (Comparative)

In this experiment, the reactor containing 0.5 ml of the 0.2 M MMAO scavenger solution and heated to 80° C., was pressurised to 8 bar with ethylene. A 0.5 ml aliquot of the catalyst premix solution, containing Composition 2, was injected into the reactor to start the reaction (Al:Cr ratio of 500:1). The reaction was stopped when the maximum uptake of ethylene was reached, 105 minutes.

The product mixture was analysed by GC. The results can be found in Table 1.

Example 6 (Comparative)

In this experiment, the reactor containing 0.5 ml of the 0.2 M MMAO scavenger solution and heated to 80° C., was pressurised to 20 bar with ethylene. However, due to the high rate of reaction exceeding the feed rate of the reactor the pressure during the reaction was only 7-10 bar. A 0.5 ml aliquot of the catalyst premix solution, containing Composition 2, was injected into the reactor to start the reaction (Al:Cr ratio of 500:1). The reaction was stopped when the maximum uptake of ethylene was reached, 96 minutes.

The product mixture was analysed by GC. The results can be found in Table 1.

Example 7 (Comparative)

In this experiment, the reactor containing 0.5 ml of the 0.2 M MMAO scavenger solution and heated to 80° C., was pressurised to 8 bar with ethylene. A 0.5 ml aliquot of the catalyst premix solution, containing Composition 2, was injected into the reactor to start the reaction (Al:Cr ratio of 500:1). The reaction was stopped after 1 hour.

The product mixture was analysed by GC. The results can be found in Table 1.

Example 8 (Comparative)

In this experiment, the reactor containing 0.35 ml of the 0.2 M MMAO scavenger solution and heated to 80° C., was pressurised to 15 bar with ethylene. A 0.35 ml aliquot of the catalyst premix solution, containing Composition 2, was injected into the reactor to start the reaction (Al:Cr ratio of 500:1). The reaction was stopped after 1 hour.

The product mixture was analysed by GC. The results can be found in Table 1.

TABLE 1

| Example | Catalyst | Pressure | Time (mins) | TON $(1\text{-}C_6)^\dagger$ | TOF $(1\text{-}C_6)^\ddagger$ | $C_{10}$ (% wt.) | $C_6$ (% wt.) | $1\text{-}C_6$ (% wt.)* | Total Product (g) |
|---|---|---|---|---|---|---|---|---|---|
| 1 | 1 | 8 | 161 | 72100 | 26900 | 15.7 | 83.1 | 98.8 | 3.65 |
| 2 | 1 | 20 | 96 | 138000 | 86250 | 9.9 | 87.8 | 94.5 | 6.63 |
| 3 | 1 | 8 | 60 | 20300 | 20300 | 1.6 | 96.8 | 98.8 | 0.88 |
| 4 | 1 | 15 | 60 | 81800 | 81800 | 8.3 | 90.6 | 99.3 | 2.66 |

TABLE 1-continued

| Example | Catalyst | Pressure | Time (mins) | TON (1-C$_6$)† | TOF (1-C$_6$)‡ | C$_{10}$ (% wt.) | C$_6$ (% wt.) | 1-C$_6$ (% wt.)* | Total Product (g) |
|---|---|---|---|---|---|---|---|---|---|
| 5** | 2 | 8 | 105 | 83200 | 47500 | 33.9 | 65.3 | 99.4 | 5.31 |
| 6** | 2 | 20 | 107 | 95200 | 53400 | 36.2 | 63.1 | 99.3 | 6.35 |
| 7** | 2 | 8 | 60 | 48200 | 48200 | 27.7 | 71.5 | 99.4 | 2.83 |
| 8** | 2 | 15 | 60 | 55100 | 55100 | 27.4 | 71.2 | 99.4 | 2.28 |

†Turn over number, TON = mol. product/mol. catalyst
‡Turn over frequency, TOF = mol. product/(mol. catalyst × time (hours))
*% of 1-hexene by weight of the C$_6$ portion of the product composition.
**Comparative example.
C$_6$ Hydrocarbons containing 6 carbon atoms.
C$_{10}$ Hydrocarbons containing 10 carbon atoms.
1-C$_6$ 1-hexene.

1 LT Batch Reactor Procedure

The 1 LT batch reactor was heated under a nitrogen atmosphere to 70° C., purged with N$_2$ three times, and evacuated under vacuum for 5 minutes. To the reactor, a solution of 250 ml of dry toluene and 1 g of MAO solution (5.11% Al in toluene) was added in order to 'pickle' the reactor for at least 2 hours at 70° C.

The toluene and MAO 'pickle' solution was removed and the reactor was evacuated for 5 minutes, maintaining the reactor temperature at 70° C. The reactor was then filled with 250 ml dry toluene again, pressurized to the reaction pressure with ethylene, and an appropriate amount of MAO scavenger was injected. The solution was then stirred for a period of at least 5 minutes at 70° C.

A catalyst premix solution was prepared by weighing 10 pmol of Composition 1, 2 or 3, adding 7.1 g of dry toluene and adding 1.59 g (3 mmol) of a MAO solution (5.11% w Al in toluene). Thus, the premix solution prepared (10 ml) contained a total of 10 μmol of Cr and 3 mmol of Al (1 mM Cr, 0.3 M Al), representing an Al:Cr ratio of 300:1.

After stirring, the trimerization reaction was started by injecting an aliquot of a catalyst premix solution into the pressurised reactor. The reactor was then heated to the reaction temperature of 80° C. The reaction was allowed to proceed for a known amount of time whilst maintaining reaction pressure, and was stopped by rapidly cooling the reactor to about 30° C. (approximately 5 minutes). The reactor content was removed from the bottom of the 1 LT Batch Reactor.

The product mixture formed was collected and weighed. A weighed amount was used for GC analysis using a hexylbenzene internal standard.

Example 9

A 10 ml aliquot of the catalyst premix solution, prepared using Composition 1, was injected into the 1 LT reactor, containing 3 mmol MAO as a scavenger (1.59 g of MAO solution). The reaction was performed at 80° C. under a 15 bar ethylene atmosphere. The reaction was stopped after 5 hours. A total of 275 litres of ethylene was consumed.

The product mixture was analysed by GC. The results can be found in Table 2.

Example 10 (Comparative)

A 2 ml aliquot of the catalyst premix solution, prepared using Composition 2, was injected into the 1 LT reactor, containing 0.6 mmol MAO as a scavenger (317 mg of MAO solution). The reaction was performed at 80° C. under a 15 bar ethylene atmosphere. After 205 minutes an extra 2 ml of the catalyst premix solution was injected. The reaction was stopped after 4.5 hours. A total of 325 litres of ethylene was consumed.

The product mixture was analysed by GC. The results can be found in Table 2.

Example 11 (Comparative)

A 2 ml aliquot of the catalyst premix solution, prepared using Composition 3 in the 57/43 mixture ratio, was injected into the 1 LT reactor, containing 0.6 mmol MAO as a scavenger (317 mg of MAO solution). The reaction was performed at 80° C. under a 15 bar ethylene atmosphere. The reaction was stopped after 3 hours. A total of 250 litres of ethylene was consumed.

The product mixture was analysed by GC. The results can be found in Table 2.

Example 12 (Comparative)

A 2 ml aliquot of the catalyst premix solution, prepared using Composition 3 in the 92/8 mixture ratio, was injected into the 1 LT reactor, containing 0.6 mmol MAO as a scavenger (317 mg of MAO solution). The reaction was performed at 80° C. under a 15 bar ethylene atmosphere. The reaction was stopped after 4.5 hours. A total of 308 litres of ethylene was consumed.

The product mixture was analysed by GC. The results can be found in Table 2.

TABLE 2

| Example | Catalyst | Time (hours) | TON (1-C$_6$)† | TOF (1-C$_6$)‡ | C$_{10}$ (% wt.) | C$_6$ (% wt.) | 1-C$_6$ (% wt.)* | Total Product (g) |
|---|---|---|---|---|---|---|---|---|
| 9 | 1 | 5 | 343000 | 68600 | 7.2 | 92.3 | 99.45 | 311.8 |
| 10** | 2 | 4.5 | 914728 | 166314 | 12.5 | 86.4 | 99.75 | 355.7 |

TABLE 2-continued

| Example | Catalyst | Time (hours) | TON (1-$C_6$)† | TOF (1-$C_6$)‡ | $C_{10}$ (% wt.) | $C_6$ (% wt.) | 1-$C_6$ (% wt.)* | Total Product (g) |
|---|---|---|---|---|---|---|---|---|
| 11** | 3 (57/43) | 3 | 1309455 | 462161 | 21.8 | 74.2 | 99.36 | 296.8 |
| 12** | 3 (92/8) | 4.5 | 1337534 | 297230 | 28.5 | 69.3 | 99.42 | 324.7 |

†Turn over number, TON = mol. product/mol. catalyst
‡Turn over frequency, TOF = mol. product/(mol. catalyst × time (hours))
*% of 1-hexene by weight of the $C_6$ portion of the product composition.
**Comparative example.
$C_6$ Hydrocarbons containing 6 carbon atoms.
$C_{10}$ Hydrocarbons containing 10 carbon atoms.
1-$C_6$ 1-hexene.

It is evident from the results in Tables 1 and 2 above that the use of a catalyst composition according to the present invention containing a ligand of formula (I) as defined hereinabove, specifically (methoxyphenyl)(phenyl) $PCH_2CH_2P$(methoxyphenyl)(phenyl), results in a reduced yield of $C_{10}$ by-product than by using, under equivalent reaction conditions, an equivalent catalyst composition containing a ligand having the formula (2-methoxyphenyl)$_2$PN ($CH_3$)P(2-methoxyphenyl)$_2$ (disclosed in the examples of US 2003/0166456 which is hereby incorporated by reference in its entirety) or a ligand having the formula (2-methoxyphenyl)(phenyl)PN($CH_3$)P(methoxyphenyl)(phenyl), neither of which fall within formula (I) as defined hereinabove.

The invention claimed is:

1. A catalyst composition suitable for the trimerization of olefinic monomers, wherein the catalyst composition comprises:
a) a source of chromium, molybdenum or tungsten;
b) a ligand of general formula (I);

$(R^1)(R^2)P—X—P(R^3)(R^4)$     (I)

wherein:
X is an ethylene bridging group which contains from 2 to 6 carbon atoms;
$R^1$ and $R^3$ are independently selected from the group consisting of optionally substituted phenyl groups which do not contain a polar substituent at any of the ortho-positions;
$R^2$ and $R^4$ are independently selected from aromatic groups, each $R^2$ and $R^4$ bearing a polar substituent on at least one of the ortho-positions; and
c) a cocatalyst.

2. The catalyst composition according to claim 1 wherein the ethylene group, X, is —$CH_2CH_2$—.

3. The catalyst composition according to of claim 1 wherein $R^2$ and $R^4$ are independently selected from the group consisting of optionally substituted phenyl groups wherein the polar substituent is a branched $C_1$-$C_{20}$ alkoxy group.

4. The catalyst composition according to claim 1 wherein $R^2$ and $R^4$ are 2-methoxyphenyl groups.

5. The catalyst composition according to claim 1 wherein the cocatalyst is selected from the group consisting of methylalumoxane and modified methylalumoxane.

6. The catalyst composition according to claim 1 wherein component a) is a source of chromium.

7. The catalyst composition according to claim 6 wherein the source of chromium is $CrCl_3$.

8. The catalyst composition according to claim 1 wherein the molar ratio of component a) to component b) is in the range of from about 10,000:1 to about 1:10,000.

9. The catalyst composition according to claim 1 wherein the molar ratio of component a) to component b) is in the range of from about 10:1 to about 1:10.

10. The catalyst composition according to claim 1 wherein the molar ratio of component a) to component b) is in the range of from about 1.5:1 to about 1:1.5.

11. The catalyst composition according to claim 1 wherein the co-catalyst is used in an amount to provide a ratio in the range from about 0.1 to about 20,000 aluminum or boron atoms per atom of chromium, molybdenum or tungsten.

12. The catalyst composition according to claim 1 wherein the co-catalyst is used in an amount to provide a ratio in the range from about 1 to about 2,000 aluminum or boron atoms per atom of chromium, molybdenum or tungsten.

13. A process for the trimerization of olefinic monomers, wherein the process comprises contacting at least one olefinic monomer under trimerization reaction conditions with a catalyst composition according to claim 1.

14. The process according to claim 13 wherein the temperature is in the range from about −100° C. to about 200° C.

15. The process according to claim 13 wherein the temperature is in the range from about 0° C. to about 150° C.

16. The process according to claim 13 wherein the temperature is in the range from about 25° C. to about 100° C.

17. The process according to claim 13 wherein the pressure is in the range of from about 0 to about 100 barg.

18. The process according to claim 13 wherein the pressure is in the range of from about 1 to about 50 barg.

* * * * *